(12) United States Patent
Hosahudya et al.

(10) Patent No.: US 7,556,808 B2
(45) Date of Patent: Jul. 7, 2009

(54) DUAL INHIBITORS OF HIV-1 GP-120 INTERACTIONS

(75) Inventors: Gopi Hosahudya, Philadelphia, PA (US); Irwin Chaiken, Gladwyne, PA (US)

(73) Assignee: Philadelphia Health and Education Corporation, Philadelphia, PA (US)

( * ) Notice: Subject to any disclaimer, the term of this patent is extended or adjusted under 35 U.S.C. 154(b) by 280 days.

(21) Appl. No.: 11/305,401

(22) Filed: Dec. 16, 2005

(65) Prior Publication Data

US 2006/0135746 A1 Jun. 22, 2006

Related U.S. Application Data

(60) Provisional application No. 60/644,172, filed on Jan. 14, 2005, provisional application No. 60/637,091, filed on Dec. 16, 2004.

(51) Int. Cl.
*A61K 39/00* (2006.01)
*A61K 39/21* (2006.01)
*A61K 38/00* (2006.01)
*A61K 39/385* (2006.01)
*C12N 33/53* (2006.01)

(52) U.S. Cl. .............. 424/184.1; 424/187.1; 424/188.1; 424/185.1; 424/194.1; 435/7.1; 530/300

(58) Field of Classification Search ........................ None
See application file for complete search history.

(56) References Cited

FOREIGN PATENT DOCUMENTS

WO WO0192549 * 6/2001

OTHER PUBLICATIONS

Ferrer M et al. "Peptide ligands to human immunodeficiency virus type 1 gp120 identified from phage display libraries". J Virol. Jul. 1999;73(7):5795-802.*
Biorn et al., "Mode of Action for Linear Peptide Inhibitors of HIV-2 gp120 Interactions", Biochemistry 2004 43:1928-1938.
Chan et al., "Core Structure of gp41 from the HIV Envelope Glycoprotein", Cell 1997 89:263-273.
Dalgleish et al., "The CD4 (T4) antigen is an essential component of the receptor for the AIDS retrovirus", Nature 1984 312 (20/27):763-767.
Deiters et al., "Adding Amino Acids with Novel Reactivity to the Genetic Code of *Saccharomyces Cerevisiae*", J. Am. Chem. Soc. 2003 125:11782-11783.
Doranz et al., "A Dual-Tropic Primary HIV-1 Isolate That Uses Fusin and the β-Chemokine Receptors CKR-5, CKR-3, and CKR-2b as Fusion Cofactors", Cell 1996 85:1149-1158.
Dragic et al., "HIV-1 entry into CD4+ cells is mediated by the chemokine receptor CC-CKR-5", Nature 1996 381:667-673.
Fazio et al., Synthesis of Sugar Arrays in Microtiter Plate, J. Am. Chem. Soc. 2002 124:14397-14402.
Feng et al., "HIV-1 Entry Cofactor:Functional cDNA Cloning of a Seven-Transmembrane, G Protein-Coupled Receptor", Science 1996 272:872-877.
Ferrer et al., "Peptide Ligands to Human Immunodeficiency Virus Type 1 gp120 Identified from Phage Display Libraries", Journal of Virology 1999 73(7):5795-5802.
Helms et al., "Dendronized Linear Polymers via Click Chemistry", J. Am. Chem. Soc. 2004 126:15020-15021.
Klatzmann et al., "T-lymphocyte T4 molecule behaves as the receptor for human retrovirus LAV", Nature 1984 312 (20/27):767-768.
Link et al., "Cell Surface Labeling of *Escherichia coli* via Copper(I)—Catalyzed [3+2] Cycloaddition", J. Am. Chem. Soc. 2003 125:11164-11165.
Lundquist et al., "A New Tri-Orthogonal Strategy for Peptide Cyclization", Organic Letters 2002 4(19):3219-3221.
Manetsch et al., "In Situ Click Chemistry:Enzyme Inhibitors Made to Their Own Specifications", J. Am. Chem. Soc. 2004 126:12809-12818.
Rostovtsev et al., "A Stepwise Huisgen Cycloaddition Process:Copper(I)—Catalyzed Regioselective "Ligation" of Azides and Terminal Alkynes", Angew. Chem. Int. Ed. 2002 41(14):2596-2599.
Speers et al., "Profiling Enzyme Activities In Vivo Using Click Chemistry Methods", Chemistry & Biology 2004 11:535-546.
Tan et al., "Atomic structure of a thermostable subdomain of HIV-1 gp41", Proc. Natl. Acad. Sci. USA 1997 94:12303-12308.
Tornøe et al., "Peptidotriazoles on Solid Phase: [1,2,3]-Triazoles by Regiospecific Copper(I)—Catalyzed 1,3-Dipolar Cycloadditions of Terminal Alkynes to Azides", J. Org. Chem. 2002 67:3057-3064.
Trkola et al., "CD4-dependent, antibody-sensitive interactions between HIV-1 and its co-receptor CCR-5", Nature 1996 384:184-187.
Wang et al., "Bioconjugation by Copper(I)—Catalyzed Azide-Alkyne [3+2] Cycloaddition", J. Am. Chem. Soc. 2003 125:3192-3193.
Wu et al., "CD4-induced interaction of primary HIV-1 gp120 glycoproteins with the chemokine receptor CCR-5", Nature 1996 384:179-183.
Wyatt et al., "The HIV-1 Envelope Glycoproteins:Fusogens, Antigens, and Immunogens", Science 1998 280:1884-1888.

* cited by examiner

*Primary Examiner*—Bo Peng
(74) *Attorney, Agent, or Firm*—Drinker Biddle & Reath LLP

(57) ABSTRACT

Compounds, which inhibit the binding of gp120 to CD4 as well as 17b and methods for their use in inhibiting the HIV fusion process, are provided.

3 Claims, 4 Drawing Sheets

X

DUAL INHIBITORS OF HIV-1 GP-120 INTERACTIONS

This patent application claims the benefit of priority to U.S. Provisional Application Ser. No. 60/644,172, filed Jan. 14, 2005 and U.S. Provisional Application Ser. No. 60/637,091, filed Dec. 16, 2004, teachings of each of which are herein incorporated by reference in their entirety.

This invention was supported in part by funds from the U.S. government (NIH Grant No. P01 GM 056550-08/C210JC) and the U.S. may have certain rights in this invention.

BACKGROUND OF THE INVENTION

Acquired immunodeficiency syndrome (AIDS), the global epidemic disease caused by HIV-1, has created an urgent need for new classes of antiviral agents (UNAIDS/World Health Organization (2003) AIDS Epidemic Update (UNAIDS—World Health Organization, Geneva)). The envelope glycoprotein of HIV-1 is a trimer consisting of three gp120 exterior envelope glycoproteins and gp41 transmembrane glycoproteins (Chan et al. Cell 1997, 89, 263-273; Wyatt et al. Science 1998, 280, 1884-1888; Tan et al. Proc. Natl. Acad. Sci. USA 1997, 94, 12303-12308). Viral infection is initiated by gp120 binding to CD4 on the host cell surface (Klatzmann et al. Nature 1984, 312, 767-768; Dalgleish et al. Nature 1984, 312, 763-767). The binding of these two proteins promotes a conformational change in gp120 that increases its affinity with a second host cell receptor, one of the chemokine receptors, CCR5 and CXCR4 (Trkola et al. Nature 1996, 384, 184-187; Feng et al. Science 1996, 872-877; Doranz et al. Cell 1996, 85, 1149-1158; Dragic et al. Nature 1996, 381, 667-673; Wu et al. Nature 1996, 384, 179-183). The interaction of gp120 with its receptors is thought to promote further conformational rearrangements in HIV-1 envelope that drive fusion of the viral and host cell membranes. Blocking of these interactions between gp120 and cell surface receptors is an attractive goal for preventing HIV-infection.

A 12-residue peptide [RINNPWSEAMM (SEQ ID NO:1)] was discovered by phage library (Ferrer et al. J. Virol. 1999, 73, 5795-5802). Its mode of action showed (Biorn et al. Biochemistry 2004, 43, 1928-1938) that, the peptide inhibited the interaction of gp120 to CD4 and 17b, an antibody that recognizes an epitope overlapping the CCR5 binding site, with micromolar affinity. The various mutations and truncations of the peptide confirmed that the entire sequence with the large aromatic residue Trp next to Pro is critical for binding.

SUMMARY OF THE INVENTION

A modified peptide with 4-phenyl, 1,4 disubstituted 1,2,3 triazole, fabricated through click chemistry, has now been identified, which inhibits the binding of gp120 to CD4 as well as 17b at $IC_{50}$ values of 22 and 29 nanomolar, respectively.

Accordingly, the present invention relates to compositions comprising this modified peptide or mutants or fragments thereof, methods for designing new antagonists based upon this peptide or mutants or fragments thereof and methods for using this peptide or mutants or fragments thereof and newly designed antagonists to inhibit the HIV fusion process.

BRIEF DESCRIPTION OF THE FIGURES

FIG. 2A provides response sensorgrams for increasing concentrations (5 nmol to 5 µmol) of peptide 5 binding to the immobilized YU2 gp120. FIG. 2B provides a fit of direct binding data to a steady state 1:1 binding model. Req. was calculated from 280 to 295 seconds in each concentration sensorgram and plotted against the concentration of the peptide. Equilibrium binding constants for YU2-peptide 5 interaction are $KA=7.99 \times 10^7$ $M^{-1}$ and $KD=1.28 \times 10^{-8}$ M.

DETAILED DESCRIPTION OF THE INVENTION

Recent advances of Cu(I)-catalyzed Huigen 1-3 dipolar cycloaddition of azides and terminal alkynes affords 1,4-disubstituted 1,2,3-triazoles with superior regioselectivity, and almost quantitative transformation under extremely mild conditions (Rostovtsev et al. Angew. Chem. Int. Ed. 2002, 41, 2596-2599; Tornoe et al. J. Org. Chem. 2002, 67, 3057-3064). The simple and robust features of this methodology have found application in drug discovery, bioconjugation and material science (Wang et al. J. Am. Chem. Soc. 2003, 125, 3192-3193; Deiters et al. J. Am. Chem. Soc. 2003, 125, 11782-11783; Link et al. J. Am. Chem. Soc. 2003, 125, 11164-11165; Speers et al. Chemistry & Biology, 2004, 11, 535-546; Fazio et al. J. Am. Chem. Soc. 2002, 124, 14397-14402; Manetsch et al. J. Am. Chem. Soc. 2004, 126, 12809-12818; Helms et al. J. Am. Chem. Soc. 2004, 126, 15020-15021).

Figure 1A:
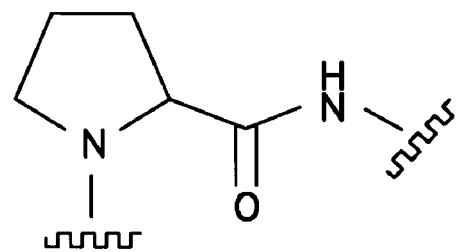
FIG. 1A shows the structure of a native peptide with proline.
Figure 1B:
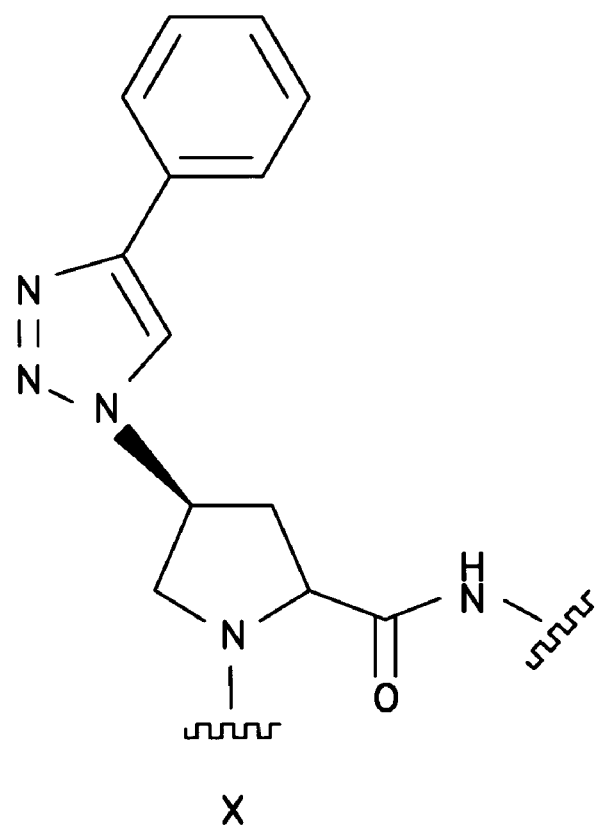
FIG. 1B shows the structure of X in peptide 5 of the present invention comprising a (2S,4S)-4-(4-phenyl-1H-1,2,3-triazol-1-yl)pyrrolidine-2-carboxylic acid) substituted proline.

In our study of the entry inhibitor, RINNIPWSEAMM (SEQ ID NO:1), we were interested in replacing proline of this peptide, referred to herein as peptide 1 (structure shown in FIG. 1A), with γ-amino proline (Amp). We used surface plasmon resonance to verify the direct interactions of peptides to YU2 gp120. Surface plasmone resonance analysis showed that peptide 4 (RINNIAmpSEAMM; SEQ ID NO:4) with cis-γ-amino proline had no effect on gp120. However, intermediate peptide 2 (RINNIHypSEAMM; SEQ ID NO:2) and intermediate peptide 3 (RINNIAzpSEAMM; SEQ ID NO:3), with trans-4-hydroxyproline (Hyp) and cis-4-azidoproline (Azp), respectively, retain the binding properties. Peptide 3 showed a marginally increased binding effect to YU2 gp120, with equilibrium constant $K_D$, 2.87 micromolar. Further, peptide 5 (RINNIXSEAMM; SEQ ID NO:5; structure of X depicted in FIG. 1B) exhibited enhanced binding affinity to gp120 and enhanced inhibition of cell surface receptor binding, as compared to the starting peptide (SEQ ID NO:1/peptide 1).

The equilibrium constant $K_D$ for all peptides 1-5, in direct binding analysis over immobilized gp120, are given in Table 1.

TABLE 1

Sequences of peptide and their direct binding kinetic constants with surface immobilized YU2 gp120

| Peptide sequence | SEQ ID NO/ Peptide Number | $K_D$ |
|---|---|---|
| RINNIPWSEAMM | SEQ ID NO:1/Peptide 1 | $4.46 \times 10^{-6}$ M |
| RINNIHypWSEAMM | SEQ ID NO:2/Peptide 2 | $23.6 \times 10^{-6}$ M |
| RINNIAzpWSEAMM | SEQ ID NO:3/Peptide 3 | $2.81 \times 10^{-6}$ M |
| RINNIAmpWSEAMM | SEQ ID NO:4/Peptide 4 | — |
| RINNIXWSEAMM | SEQ ID NO:5/Peptide 5 | $8-13 \times 10^{-9}$ M |

The peptides were synthesized using Fmoc-chemistry on PAL-PEG-PS resin. The trans-4-hydroxyl group of proline in peptide 2 was converted to peptide 3 through the trans-4-mesylate, followed by azide displacement. The cis-4-azido group on proline was converted to cis-4-amine using trimethylphosphine, dioxane water mixture (Lundquist et al. Org. Lett. 2002, 4, 3219-3221). The [3+2] cycloaddition reaction was carried out on resin. The resin was suspended in acetonitrile, water, DIEA and pyridine (4:4:2:1) mixture. The phenylacetylene was added followed by a catalytic amount CuI. The peptide was cleaved from the resin using TFA. The peptides were synthesized individually for large quantities.

Additional experiments were conducted with peptide 5.

Figure 2A:
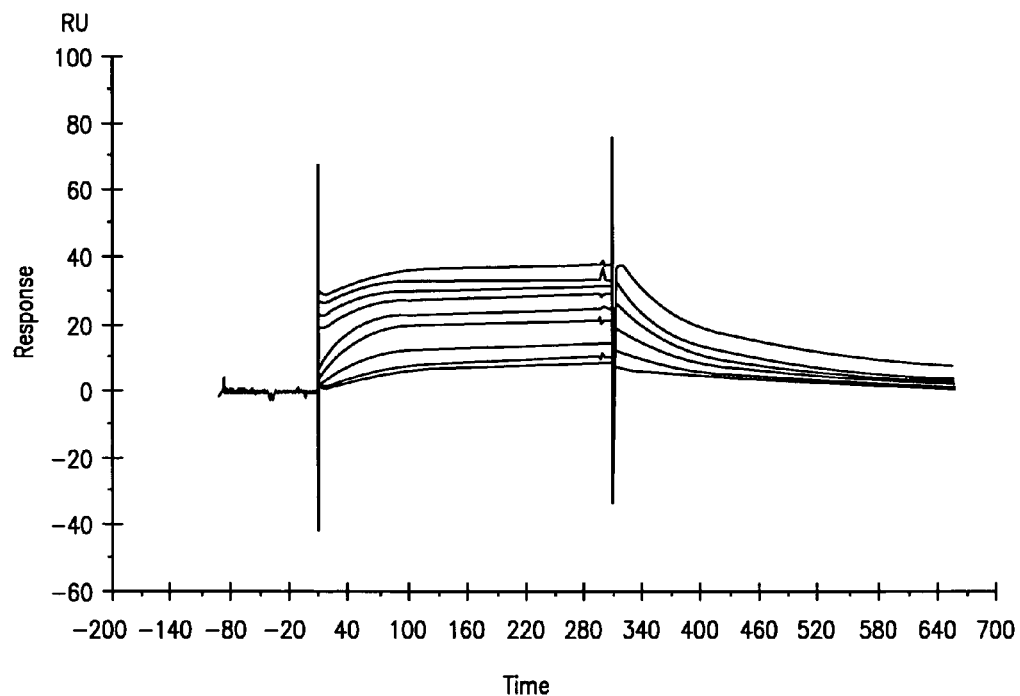
FIGS. 2A and 2B are line graphs from experiments measuring direct binding of peptide 5 over immobilized YU2 gp120.
Figure 2B:
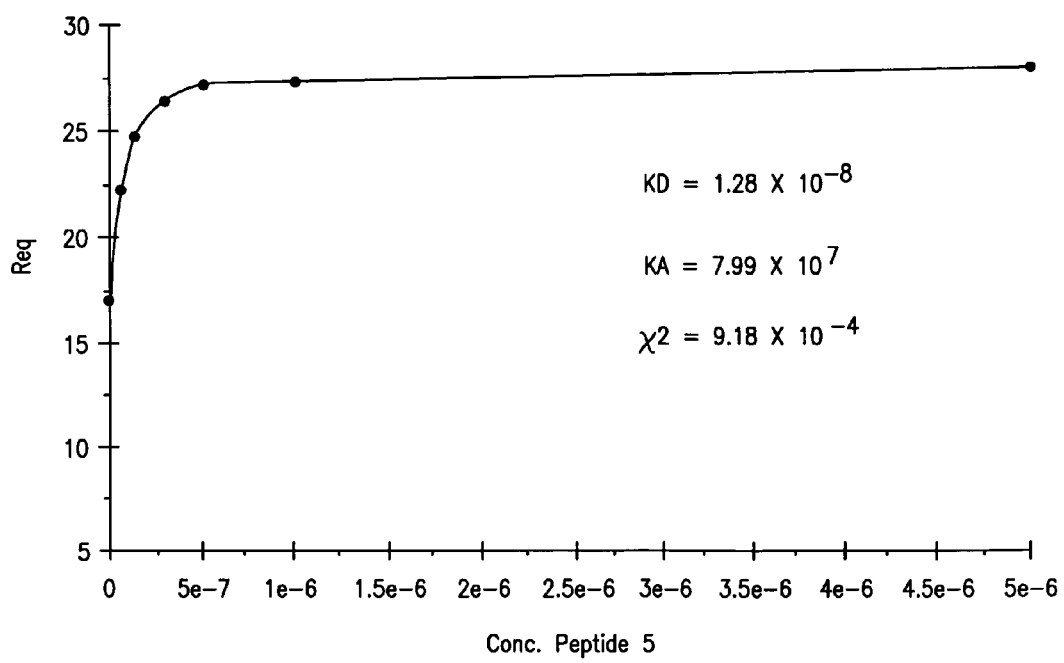

Increasing concentrations of peptide were passed over an immobilized high density (5000 RU) surface. FIG. 2 shows the direct binding of peptide 5 YU2 gp120. Buffer injections and controls were subtracted for all reported data. The equilibrium constant $K_D$ was calculated from the fit of direct binding to a steady state 1:1 binding model as a function of Req. (280 to 295 seconds of each curve) vs. concentration peptide 5.

To assess the inhibition of binding of gp120 to CD4 and 17b, the analyte YU2 gp120 (100 nmol) in the absence or presence of peptide 5 was passed over immobilized CD4, 17b and control 2B6R Fab. The peptide 5 exhibited no direct binding to CD4, 17b or control 2B6R.

Figure 3A:
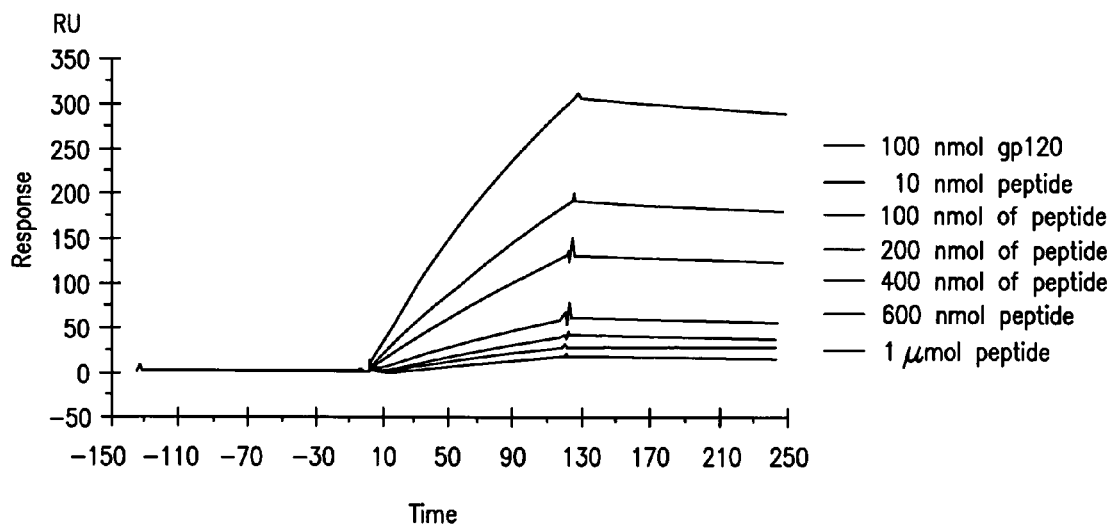
FIGS. 3A and 3B are response sensorgrams of complete inhibition of binding experiments of YU2 gp120 to CD4 (FIG. 3A) and 17b (FIG. 3B) by peptide 5. The CD4 and 17b were immobilized on a CM5 sensor chip. YU2 gp120 (100 nmol) was passed over the surface in the absence or presence of 10 nmol to 1 µmol of peptide 5.
Figure 3B:
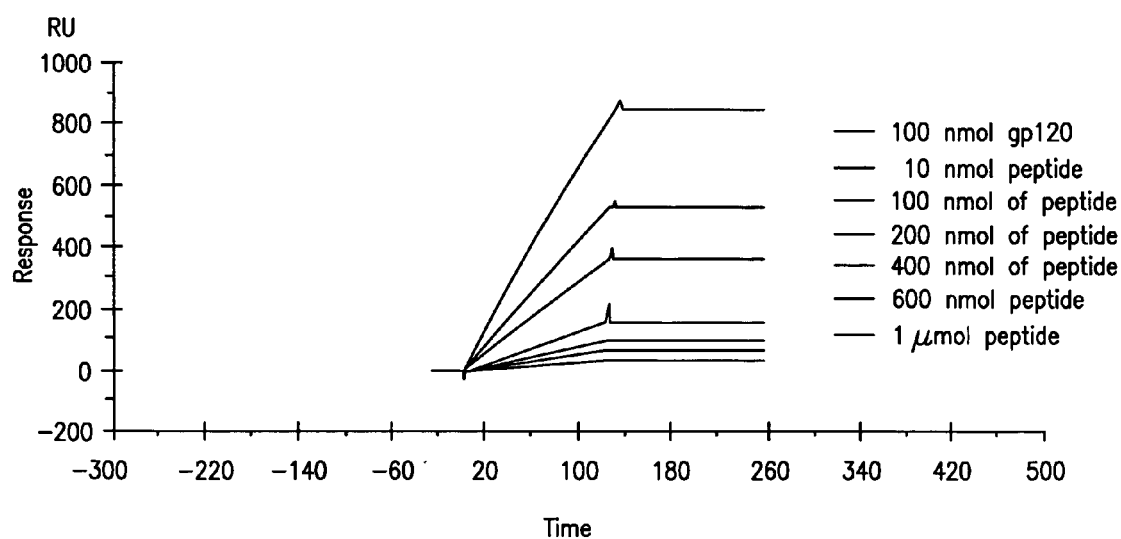

FIG. 3 shows that increasing concentration of peptide 5 from 0 to 1 micromolar leads to almost complete inhibition of binding of gp120 to both sCD4 and 17b surfaces. The $IC_{50}$ values for peptide 5 inhibition of binding to YU2 gp120 to sCD4 and 17b were calculated by using the fraction of the initial rate (6-20s) of YU2 gp120 binding in the presence verses absence of peptide 5 and plotting these against the log of peptide concentration.

Figure 4:
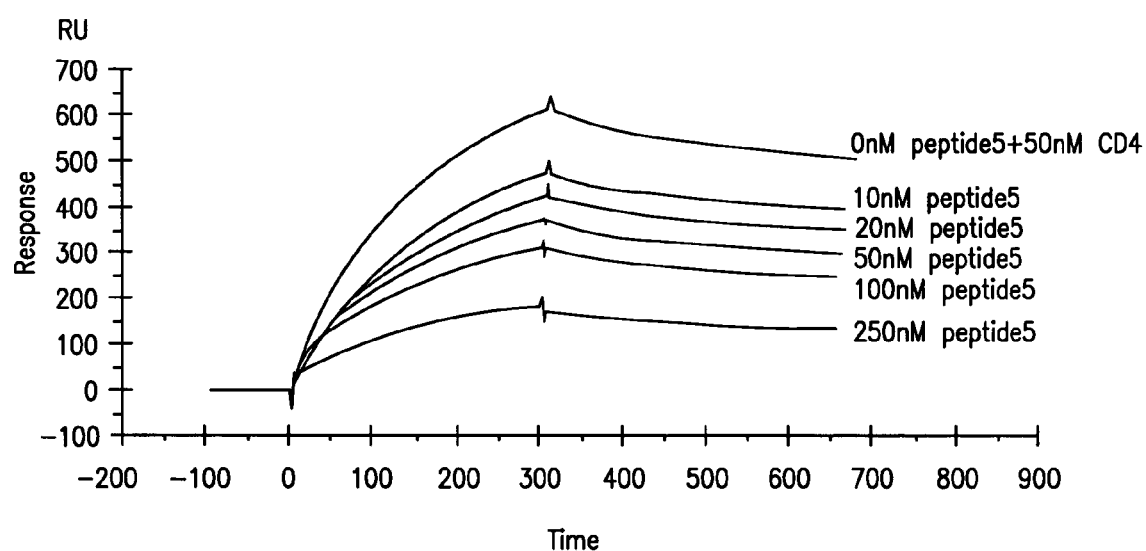
FIG. 4 is a response sensorgram of peptide 5 competition with CD4 in the reverse orientation over immobilized YU2 gp120. CD4 (50 nM) was passed over a high-density YU2 gp120 surface in absence or presence of 10 to 250 nM of peptide 5.

Using the same high density gp120 surface, we confirmed the inhibition in the reverse orientation. FIG. 4 shows the inhibition of binding of 100 nmol sCD4 to surface immobilized gp120 by increasing concentrations of peptide 5.

Thus, as demonstrated herein, peptide 5 (FIG. 1B) comprising a cis-γ-substituted proline (2S,4S)-4-(4-phenyl-1H-1,2,3-triazol-1-yl)pyrrolidine-2-carboxylic acid) strongly inhibits the interaction of gp120 to both CD4 and 17b with similar $IC_{50}$ values or 23 and 29 nmol, respectively. The results with this peptide encourage its utilization in inhibiting the HIV fusion process and as a lead tool in the drug discovery process. Mutants as well as fragments of peptide 5 are also expected to exhibit similar properties as described herein. The strong (close to nanomolar) inhibition of binding of gp120 by peptide 5 to both host cell receptors is indicative of its utility as an antagonist of the HIV-1 fusion process and in designing new compounds, including, but not limited to, mutants of peptide 5, fragments of peptide 5 and small organic molecule antagonists of the HIV-1 fusion process.

What is claimed is:

1. An isolated peptide consisting of SEQ ID NO: 5.
2. A composition comprising the peptide of claim 1.
3. A method of inhibiting the binding of HIV to cell surface receptor CD4, said method comprising contacting cells infected with HIV with the composition of claim 2.

* * * * *

UNITED STATES PATENT AND TRADEMARK OFFICE
CERTIFICATE OF CORRECTION

PATENT NO.        : 7,556,808 B2
APPLICATION NO.   : 11/305401
DATED             : July 7, 2009
INVENTOR(S)       : Gopi et al.

It is certified that error appears in the above-identified patent and that said Letters Patent is hereby corrected as shown below:

On page 1, line 9 of the specification please amend to read:

--This invention was made with government support under National Institutes of Health Grant No. P01 GM 056550-08/C210JC. The government has certain rights under the invention.--

Signed and Sealed this

First Day of December, 2009

David J. Kappos
*Director of the United States Patent and Trademark Office*

SEQUENCE LISTING

<160> NUMBER OF SEQ ID NOS: 5

<210> SEQ ID NO 1
<211> LENGTH: 12
<212> TYPE: PRT
<213> ORGANISM: Artificial sequence
<220> FEATURE:
<223> OTHER INFORMATION: Synthetic

<400> SEQUENCE: 1

Arg Ile Asn Asn Ile Pro Trp Ser Glu Ala Met Met
1               5                   10

<210> SEQ ID NO 2
<211> LENGTH: 12
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X=trans-4-hydroxyproline

<400> SEQUENCE: 2

Arg Ile Asn Asn Ile Xaa Trp Ser Glu Ala Met Met
1               5                   10

```
<210> SEQ ID NO 3
<211> LENGTH: 12
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X=cis-4-azidoproline

<400> SEQUENCE: 3

Arg Ile Asn Asn Ile Xaa Trp Ser Glu Ala Met Met
1               5                   10

<210> SEQ ID NO 4
<211> LENGTH: 12
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X=cis-gamma-amino proline

<400> SEQUENCE: 4

Arg Ile Asn Asn Ile Xaa Trp Ser Glu Ala Met Met
1               5                   10

<210> SEQ ID NO 5
<211> LENGTH: 12
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X=(2S,4S)-4-(4-phenyl-1H-1,2,3-triazol-1-yl)
      pyrrolidine-2-carboxylic acid)

<400> SEQUENCE: 5

Arg Ile Asn Asn Ile Xaa Trp Ser Glu Ala Met Met
1               5                   10
```